(12) United States Patent
Carey et al.

(10) Patent No.: US 8,874,214 B2
(45) Date of Patent: Oct. 28, 2014

(54) IMPLANTABLE PULSE GENERATOR WITH A STACKED CAPACITOR, BATTERY, AND ELECTRONICS

(75) Inventors: Bart A. Carey, Roseville, MN (US);
James E. Blood, Shoreview, MN (US);
Steven J. Meyer, St. Paul, MN (US);
Gregory J. Sherwood, North Oaks, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1218 days.

(21) Appl. No.: 11/467,808

(22) Filed: Aug. 28, 2006

(65) Prior Publication Data

US 2008/0091246 A1 Apr. 17, 2008

(51) Int. Cl.
*A61N 1/375* (2006.01)
*H01M 16/00* (2006.01)
*H01M 2/10* (2006.01)
*A61N 1/378* (2006.01)

(52) U.S. Cl.
CPC ............... *A61N 1/375* (2013.01); *H01M 16/00* (2013.01); *Y02E 60/12* (2013.01); *A61N 1/378* (2013.01); *H01M 2/1066* (2013.01)
USPC .......................... 607/36; 607/4; 607/5; 607/9

(58) Field of Classification Search
USPC ............................... 607/4, 5, 9, 36
See application file for complete search history.

(56) References Cited

U.S. PATENT DOCUMENTS

| | | | |
|---|---|---|---|
| 3,993,508 A | 11/1976 | Erlichman | |
| 4,113,921 A | 9/1978 | Goldstein et al. | |
| 4,254,775 A | * 3/1981 | Langer | ............................. 607/5 |
| 5,131,388 A | 7/1992 | Pless et al. | |
| 5,370,663 A | 12/1994 | Lin | |
| 5,370,669 A | 12/1994 | Daglow et al. | |
| 5,522,851 A | 6/1996 | Fayram | |
| 5,749,911 A | 5/1998 | Westlund | |

(Continued)

FOREIGN PATENT DOCUMENTS

| | | |
|---|---|---|
| JP | 2001-513679 A | 9/2001 |
| JP | 2002-509008 A | 3/2002 |

(Continued)

OTHER PUBLICATIONS

Kelley, Shawn, et al., "Method and Apparatus for Porous Insulative Film for Insulating Energy Source Layers", U.S. Appl. No. 11/127,025, filed May 11, 2005, 21 Pages.

(Continued)

*Primary Examiner* — Carl H Layno
*Assistant Examiner* — Jennifer Ghand
(74) *Attorney, Agent, or Firm* — Schwegman Lundberg & Woessner, P.A.

(57) ABSTRACT

One embodiment of the present subject matter includes an implantable medical device which includes a first power source comprising a first plurality of substantially planar electrodes, the first power source including at least a first power source face, an electronics module including a first substantially planar electronics face, and a second electronics face opposed to the first substantially planar electronics face, with the first substantially planar electronics face adjacent to, and substantially coextensive with, the first power source face and a second power source comprising a second plurality of substantially planar electrodes, the second power source positioned adjacent to and adapted to interface with the second electronics face.

14 Claims, 7 Drawing Sheets

(56) References Cited

U.S. PATENT DOCUMENTS

| | | |
|---|---|---|
| 5,954,751 A | 9/1999 | Chen et al. |
| 6,010,317 A | 1/2000 | Maget et al. |
| 6,185,452 B1 | 2/2001 | Schulman et al. |
| 6,330,925 B1 | 12/2001 | Ovshinsky et al. |
| 6,388,866 B1 | 5/2002 | Rorvick et al. |
| 6,445,948 B1 | 9/2002 | Somdahl et al. |
| 6,459,566 B1 | 10/2002 | Casby et al. |
| 6,498,951 B1 | 12/2002 | Larson et al. |
| 6,522,525 B1 | 2/2003 | O'Phelan et al. |
| 6,556,863 B1 | 4/2003 | O'Phelan et al. |
| 6,674,634 B2 | 1/2004 | O'Phelan et al. |
| 6,678,559 B1 | 1/2004 | Breyen et al. |
| 6,699,265 B1 | 3/2004 | O'Phelan et al. |
| 6,721,602 B2 | 4/2004 | Engmark et al. |
| 6,799,072 B2 | 9/2004 | Ries et al. |
| 6,881,516 B2 | 4/2005 | Aamodt et al. |
| 6,885,887 B2 | 4/2005 | O'Phelan et al. |
| 6,963,482 B2 | 11/2005 | Breyen et al. |
| 7,479,349 B2 | 1/2009 | O'Phelan et al. |
| 7,917,207 B2 | 3/2011 | Youker |
| 8,055,346 B2 | 11/2011 | Youker |
| 8,406,882 B2 | 3/2013 | Youker |
| 2002/0161404 A1 | 10/2002 | Schmidt |
| 2003/0072124 A1* | 4/2003 | O'Phelan et al. .......... 361/301.4 |
| 2003/0165744 A1 | 9/2003 | Schubert et al. |
| 2003/0204216 A1 | 10/2003 | Ries et al. |
| 2004/0127952 A1 | 7/2004 | O'Phelan et al. |
| 2004/0220627 A1 | 11/2004 | Crespi et al. |
| 2004/0230250 A1 | 11/2004 | Neumann et al. |
| 2005/0041366 A1 | 2/2005 | Breven et al. |
| 2005/0052825 A1 | 3/2005 | O'Phelan |
| 2005/0154423 A1 | 7/2005 | Goedeke et al. |
| 2005/0221171 A1 | 10/2005 | Haasl et al. |
| 2005/0264979 A1 | 12/2005 | Breyen et al. |
| 2006/0012942 A1 | 1/2006 | Poplett |
| 2006/0023400 A1 | 2/2006 | Sherwood |
| 2006/0247715 A1 | 11/2006 | Youker |
| 2009/0025207 A1 | 1/2009 | Youker |
| 2009/0123825 A1 | 5/2009 | O'Phelan et al. |
| 2010/0203380 A1 | 8/2010 | O'Phelan et al. |
| 2011/0160812 A1 | 6/2011 | Youker |
| 2012/0045668 A1 | 2/2012 | Youker |

FOREIGN PATENT DOCUMENTS

| | | |
|---|---|---|
| JP | 2005-523129 A | 8/2005 |
| JP | 2006-512745 A | 4/2006 |
| JP | 5089698 | 9/2012 |
| WO | WO-98/37926 A | 9/1998 |
| WO | WO-99/36126 A1 | 7/1999 |
| WO | WO-03/090862 A1 | 11/2003 |
| WO | WO-2004/062009 A2 | 7/2004 |
| WO | WO-2005070498 A1 | 8/2005 |
| WO | WO-2008/027639 A2 | 3/2008 |

OTHER PUBLICATIONS

O'Phelan, Michael J., "Batteries Including a Flat Plate Design", U.S. Appl. No. 60/437,537, filed Dec. 31, 2002, 116 Pages.

Sherwood, Gregory J., "Method and Apparatus for Single High Voltage Design Aluminum Capacitor Design", U.S. Appl. No. 60/588,905, filed Jul. 16, 2004, 241 pgs.

Youker, Nick A., "Method and Apparatus for an Implantable Pulse Generator With a Stacked Battery and Capacitor", U.S. Appl. No. 11/117,952, filed Apr. 29, 2005, 21 Pages.

"U.S. Appl. No. 11/117,952, Non-Final Office Action Mailed Sep. 25, 2007", 9 pgs.

"U.S. Appl. No. 11/117,952, Response filed Dec. 26, 2007 to Non-Final Office Action mailed Sep. 25, 2007", 9 pgs.

"U.S. Appl. No. 11/117,952, Response filed Aug. 24, 2007 to Restriction Requirement mailed Jul. 24, 2007", 7 pgs.

"U.S. Appl. No. 11/117,952, Restriction Requirement mailed Jul. 24, 2007", 6 pgs.

"U.S. Appl. No. 11/117,952, Final Office Action mailed Apr. 24, 2008", 10 pgs.

"International Application No. PCT/US2007/070697, International Search Report mailed Mar. 4, 2008", 4 pgs.

"International Application No. PCT/US2007/070697, Written Opinion mailed Mar. 4, 2008", 8 pgs.

"U.S. Appl. No. 12/178,876, Restriction Requirement mailed Jul. 14, 2009", 6 pgs.

"U.S. Appl. No. 12/178,876, Non-Final Office Action mailed Dec. 31, 2009", 9 Pgs.

"U.S. Appl. No. 12/178,876, Response filed Aug. 14, 2009 to Restriction Requirement mailed Jul. 14, 2009", 7 pgs.

"U.S. Appl. No. 12/178,876 Notice of Allowance mailed Jul. 27, 2010", 6 pgs.

"U.S. Appl. No. 12/178,876, Response filed Apr. 30, 2010 to Non Final Office Action mailed Dec. 31, 2009", 9 Pgs.

"U.S. Appl. No. 12/178,876, Notice of Allowance mailed Nov. 17, 2010", 6 pgs.

"U.S. Appl. No. 12/178,876, Preliminary Amendment mailed Jan. 21, 2009", 7 pgs.

"U.S. Appl. No. 13/285,111, Non Final Office Action mailed Apr. 3, 2012", 8 pgs.

"Japanese Application Serial No. 2009-526779, Office Action mailed Apr. 13, 2012", (w/ English Translation), 13 pgs.

"Japanese Application Serial No. 2009-526779, Response filed Jul. 13, 2012 to Office Action mailed Apr. 13, 2012", (w/ English Translation of Amended Claims), 10 pgs.

"U.S. Appl. No. 13/041,651, Notice of Allowance mailed Sep. 6, 2011", 5 pgs.

"U.S. Appl. No. 13/285,111, Notice of Allowance mailed Nov. 28, 2012", 5 pgs.

"U.S. Appl. No. 13/285,111, Response filed Aug. 2, 2012 to Non Final Office Action mailed Apr. 3, 2012", 16 pgs.

* cited by examiner

IMPLANTABLE PULSE GENERATOR WITH A STACKED CAPACITOR, BATTERY, AND ELECTRONICS

CROSS REFERENCE TO RELATED APPLICATIONS

The following commonly assigned U.S. Patents are related to the present application and are incorporated herein by reference in their entirety: "High- Energy Capacitors for Implantable Defibrillators," U.S. Pat. No. 6,556,863, filed Oct. 2, 1998, issued Apr. 29, 2003; "Flat Capacitor for an Implantable Medical Device," U.S. Pat. No. 6,699,265, filed Nov. 3, 2000, issued Mar. 2, 2004; "Method and Apparatus for Single High Voltage Aluminum Capacitor Design," U.S. Pat. No. 7,224,575, filed Jul. 15, 2005, issued May 29, 2007, which claims the benefit under 35 U.S.C 119(e) of U.S. Provisional Application Ser. No. 60/588,905, filed Jul. 16, 2004; "Batteries Including a Flat Plate Design," U.S. Pat. No. 7,479,349, filed Feb. 7, 2003, issued Jan. 20, 2009, which claims the benefit under 35 U.S.C. 119(e) of U.S. Provisional Application Ser. No. 60/437,537, filed Dec. 31, 2002. Further, the present application is related to the following commonly assigned U.S. Patent Application which is incorporated herein by reference in its entirety: "Method and Apparatus for Implantable Pulse Generator with a Stacked Battery and Capacitor," Ser. No. 11/117,952, filed Apr. 29, 2005, now abandoned.

TECHNICAL FIELD

This document relates generally to the packaging of electrical components, and more particularly, to an implantable pulse generator with a stacked capacitor, battery and electronics.

SUMMARY

The above-mentioned problems and others not expressly discussed herein are addressed by the present subject matter and will be understood by reading and studying this specification.

One embodiment of the present subject matter includes an implantable medical device which includes a first power source comprising a first plurality of substantially planar electrodes, the first power source including at least a first power source face, an electronics module including a first substantially planar electronics face, and a second electronics face substantially opposed to the first substantially planar electronics face and a second power source comprising a second plurality of substantially planar electrodes, wherein the first power source, the electronics module, and the second power source are arranged such that the first substantially planar electronics face is adjacent to, and substantially coextensive with, the first power source face, and the second power source is positioned adjacent to, and adapted to interface with, the second electronics face.

Another embodiment of the present subject matter includes a method of assembling an implantable medical device which includes layering into a stack a first power source including a first power source face, a second power source, and an electronics module including an electronics module face, such that a first power source face is substantially coextensive with a first electronics module face perimeter and encapsulating the stack with at least a first housing portion and a second housing portion which opposes the first housing portion, the first and second housing portions at least partially defining an interior, wherein the first housing portion is selected from a plurality of housing portions based on a thickness of the stack.

One embodiment of the present subject matter includes electronics module means for generating electrical pulses, a hermetically sealed implantable device housing in which the electronics module is disposed and battery means and capacitor means for layering into a stack with the electronics module means such that the stack thickness correlates to the thickness of the housing, wherein the stack is disposed in the hermetically sealed implantable device housing.

The present subject matter optionally includes embodiments in which a power source is shaped to receive a component from an adjacent layer. For example, some embodiments include a power source which has a recess shaped to receive a transformer sticking up from an electronics module. The present subject matter includes embodiments where a battery and a capacitor sandwich an electronics module. Embodiments are includes in which a stack has a profile which is substantially smooth.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

BACKGROUND

There is an ongoing interest in making electronic devices physically smaller. For devices which are implanted, smaller size is preferred both for patient comfort and for ease of implantation. Consequently, efficient packaging is a persistent design objective.

Additional objectives impact designs. Among these is manufacturing flexibility. Existing device designs require expensive tooling adjustments when a design is changed. For example, implanted devices must be extensively redesigned if an application requires an increase in energy storage ability. Improvement could be realized by a design which allows adjustment while reducing expenses associated with manufacturing, including tooling, warehousing, and other costs.

DETAILED DESCRIPTION

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

Implantable devices are used to provide a range of therapies. Embodiments of the present subject matter include implantable devices. In some of these embodiments, the devices include one or more power sources. In various embodiments, a power source is a battery. In additional embodiments, a power source is a capacitor. In various embodiments, a battery and a capacitor are used together to provide therapy. In some embodiments, a battery and a capacitor are used independent of one another to provide therapy. Some embodiments manage the power from these power sources using electronics. Often, the electronics are packaged together into a module, which can, but is not required to, include integrated circuits, circuit boards, and related electronics and packaging structures. The components of an implantable device can be largely divided into these three subcomponent groups. In various embodiments, these three subcomponent groups are interconnected and packaged into a housing of an implantable device.

Several factors relating to these components affect overall device size. The size and shape of a battery which supplies sufficient power to operate the device is one factor which affects device size. Capacitor size and electronics module size additionally affect device size. The present subject matter offers more flexibility in size of an implantable device by providing adjustability of a battery and/or a capacitor while reducing empty space in an implantable device. Further, the present subject matter provides for reduced costs related to manufacturing which can result from adjusting device size.

Figure 1A:
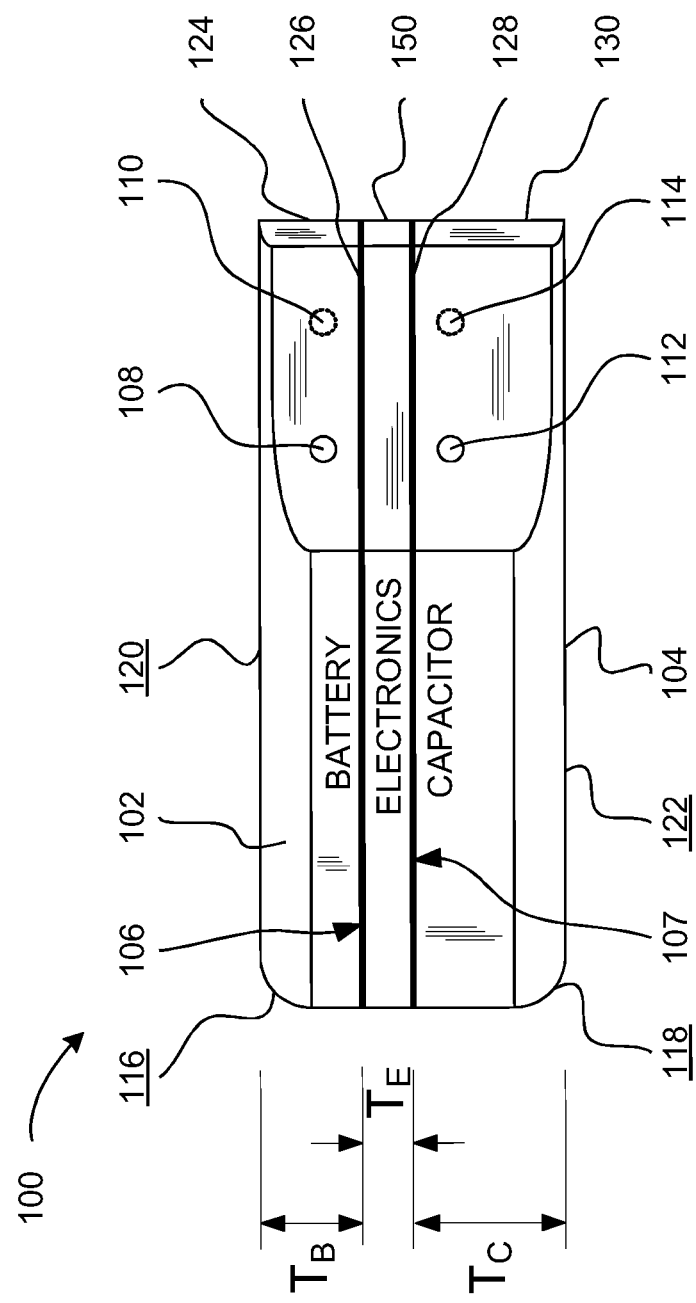
FIG. 1A is a side view of a stack of components, according to one embodiment of the present subject matter.

FIG. 1A is a side view of a stack 100 of components, according to one embodiment of the present subject matter. The stack includes a battery 102, an electronics module 150, and a capacitor 104. The stack orientation in which the electronics module 150 is sandwiched between a battery 102 and a capacitor 104 is one embodiment of a stack, and stacks including those components in different sequences are additionally contemplated by the present subject matter.

In various embodiments, the battery 102 includes a plurality of substantially planar electrodes which are stacked in alignment and packaged in a housing. Some of these embodiments use electrodes which are foils. In further embodiments, the capacitor 104 includes a plurality of substantially planar electrodes which are stacked in alignment and packaged in a housing, as shown in the illustration. Some of these embodiments use electrodes which are foils. The present subject matter includes these embodiments, but additionally includes other embodiments, such as embodiments including jelly-roll configurations for the battery and/or the capacitor.

Electrodes stack of the present subject matter, in various embodiments, are shaped substantially similar to one another. In some embodiments, anode electrode layers are shaped substantially similar to other anode electrode layers. In some embodiments, cathode layers are shaped substantially similar to other cathode electrode layers. In some embodiments, a stack of electrodes is stacked along a first vector, with the plane of the layer being orthogonal to the first vector. In various embodiments, the electrode layers are substantially constant in a distance measured orthogonally between the first vector and the electrode layer perimeter. In various embodiments, the electrode layers vary in distance measured orthogonally between the first vector and the electrode layer perimeter. As such, in some embodiments, the cross section of the stack, when sectioned along the first vector, is nonlinear. In these embodiments, the profile of the stack is not parallel to the first vector along at least some of the profile. In some embodiments, the cross section of the stack, when sectioned along the first vector, is linear, with at least some of a profile being parallel to the first vector.

The illustration incorporates a plate shaped battery 102 and a plate shaped capacitor 104, which are sandwich an electronics module 150. The presentation of these shapes is not exhaustive of exclusive of the present subject matter. Shapes are contemplated by the present subject matter which are shaped differently than those illustrated in this application, and those shapes presented herein are for demonstration purposes only.

Further, the present subject matter contemplates multiple stack configurations. The present subject matter includes multiple embodiments which include a stack of a capacitor, battery, and electronics. Some of these embodiments include a first layer and a second layer, in which the first layer abuts the second layer. Additionally, some embodiments include a first layer and a second layer in which there is a distance between the first layer and the second layer. In some of these embodiments, an element is disposed between the first layer and the second layer. For example, in some embodiments, a separator 126 is disposed between a battery 102 and an electronics module 150. The element 126 can be separator, or it can be another material. Insulative materials, as well as conductive materials, are contemplated by the present subject matter. In some embodiments the present subject matter includes a separator 128 disposed between a capacitor 104 and an electronics module 150. The element 128 can be separator, or it can be another material. Insulative materials, as well as conductive materials, are contemplated by the present subject matter.

In addition to embodiment in which a first stack layer is separated from a second stack layer by a distance by an element are embodiments in which the first layer and the second layer are separated by an air gap. In some of these embodiment, the first layer and the second layer at least partially abut. In some embodiments, a first layer is adapted to interface with a second layer. In some of these embodiments, a first layer includes bosses, cut outs, slots, or other features which can either accommodate an intended area of air gap, or which can accommodate a feature of a mating layer. As an example, consider a first layer with a boss, and a second layer including a recess which is large enough to at least accommodate the boss when the first layer and the second layer are in a stack. This is but one example of a first and second layer configuration, and other configurations are contemplated by the present subject matter.

Some embodiments include optional features which are intended to improve performance in some applications. For example, in some embodiments of the present subject matter, a battery 102 includes a contour 116, which allows for positioning the battery 102 in various devices. For example, in various embodiments, battery 102 is shaped for placement in device which has a curved exterior and a matching curved interior, such that the device is compatible with chronic implantation.

In some embodiments, the battery 102 includes a feedthrough port 108, which is adapted for passage of one or more conductors. In various embodiments, the conductors at the feedthrough port 108 are connected to the battery anode. Some embodiments additionally include a feedthrough port 110 which, in various embodiments, is connected to the battery cathode. The relationship between the case, the feedthrough ports, and the anode and cathode polarity is provided for demonstration only. The present subject matter additionally includes embodiments in which the polarity of the anode and the cathode, in relation to the stack 100, is reversed. In some embodiments, a single feedthrough port is used instead of two feedthrough ports. In these embodiments, a battery case serves as a terminal for one of the electrodes. Other embodiments include one or more feedthrough ports and a backfill port.

In various embodiments, the example capacitor 104 includes a contour 118, which allows for positioning the capacitor 104 in various devices. For example, in various embodiments, capacitor 104 is shaped for placement in device which has a curved exterior and a matching curved interior, such that the device is compatible with chronic implantation.

Some embodiments include a capacitor 104 which includes a feedthrough port 112, which is adapted for passage of one or more conductors. In various embodiments, the conductors at the feedthrough port 112 comprise a portion of the anode of the capacitor. Some embodiments additionally include a capacitor 104 which includes a feedthrough port 114. In some embodiments, feedthrough port 114 is connected to a battery cathode. The relationship between the case, the feedthrough ports, and the anode and cathode polarity is provided for demonstration only. The present subject matter additionally includes embodiments in which the polarity of the anode and the cathode, in relation to the stack 100, is reversed. In some embodiments, a single feedthrough port is used instead of two feedthrough ports. Other embodiments include one or more feedthrough ports and a backfill port.

In various embodiments, a device housing into which a battery and capacitor may be disposed has an interior. In some of these embodiments, the device interior has a first major interior face and a second major interior face. Battery and capacitor combinations can be shaped to mate to these faces. For example, in one embodiment, a battery face 120 is adapted for abutting an interior face of a housing. In some embodiments, the housing and the battery face 120 are separated from a housing by an insulator. The capacitor includes a face 122 which also is adapted for abutting an interior surface of a housing. In some embodiments, the housing and the capacitor face 122 are separated from a housing by an insulator. Sidewall 124 and sidewall 130 are adapted for placement adjacent additional device components, in various embodiments. Such device components include, but are not limited to, structures which interconnect the stack to a device feedthrough. The ports 108, 110, 112, and 114 can be positioned elsewhere on the stack 100 without departing from the present subject matter, and the illustrated configuration should be considered only as an example provided to aid in explanation.

Various embodiments maintain a continuous surface from sidewall 124 to sidewall 128. In various embodiments, the surface is smooth. In various embodiments, the interface 106 defined by the adjacent battery 102 and electronics module 150. Thus, in various embodiments, the combined battery and electronics module 150 are adapted for space efficient placement in a housing. The interface 107 between capacitor 104 and the electronics module 150 additionally extends along a continuous surface, in various embodiments. In various embodiments, the surface is smooth. As such, various embodiments, an aligned stack demonstrates an overall form factor which is substantially continuous. In various embodiments, the surface is smooth. In various embodiments, this form factor is curvilinear. In additional embodiments, the form factors is curved. In some embodiments, the housing is only marginally larger than the combined capacitor, battery, and electronics module so that the housing may accommodate those components. As such, various embodiments enable packaging additional devices in the housing adjacent the battery capacitor combination.

In various embodiments, the present subject matter includes a stack 100 which includes a battery 102 and an electronics module 150, each of which includes at least one planar face. In various embodiments, including the illustrated embodiment, the battery 102 and the electronics module 150 include two planar faces which are adjacent and which are substantially coextensive. In some of these embodiments, the battery 102 and the electronics module 150 abut. Further, in various embodiments, the present subject matter includes a stack 100 which has a capacitor 104 and an electronics module 150, each of which includes at least one planar face. In various embodiments, including the illustrated embodiment, the capacitor 104 and the electronics module 150 each include two planar faces which are adjacent and which are substantially coextensive. In some of these embodiments, the capacitor 104 and the electronics module 150 abut. The present subject includes these recitations, but is not limited as such, as other orientations are contemplated, including orientations in which a battery 102 and a capacitor 104 include respective substantially planar faces which abut, and which are substantially coextensive. The present subject matter additionally reaches embodiments in which the battery 102 and the electronics module 150 include planar faces which are adjacent and which are not substantially coextensive. The present subject matter additionally reaches embodiments in which the capacitor 104 and the electronics module 150 include planar faces which are adjacent and which are not substantially coextensive.

Battery 102 has a thickness $T_B$, in various embodiments. In various embodiments, the thickness is measured orthogonally, extending between interface 106 and surface 120. Additionally, capacitor 104 has a thickness $T_C$, in various embodiments. The thickness $T_C$ is measured orthogonally, extending between interface 107 and surface 122, in various embodiments. Battery 102 has a thickness $T_B$, in various embodiments. In various embodiments, the thickness $T_B$ is measured orthogonally, extending between interface 106 and surface 120. Electronics module 150 has a thickness $T_E$, in various embodiments. In various embodiments, the thickness $T_E$ is measured orthogonally, extending between interface 106 and interface 107.

In various embodiments, the thicknesses $T_B$ and $T_C$ are selectable to fill the volume of a device housing. For example, in one embodiment, the present subject matter creates an index of a plurality of flat capacitors, the index created by measuring the thickness $T_C$ of each flat capacitor and storing that thickness in a first index. Additionally, in various embodiments, the present subject matter creates an index of a plurality of flat batteries, the index created by measuring the thickness $T_B$ of each flat battery and storing that thickness in a second index. The present subject matter than selects a battery and a capacitor including respective thicknesses $T_B$, $T_C$ selected to fill the volume of the targeted device housing.

In additional embodiments, the thickness of the battery $T_B$ is based on application requirements. Further, the thickness of the battery $T_C$ is based on application requirements.

Figure 1B:
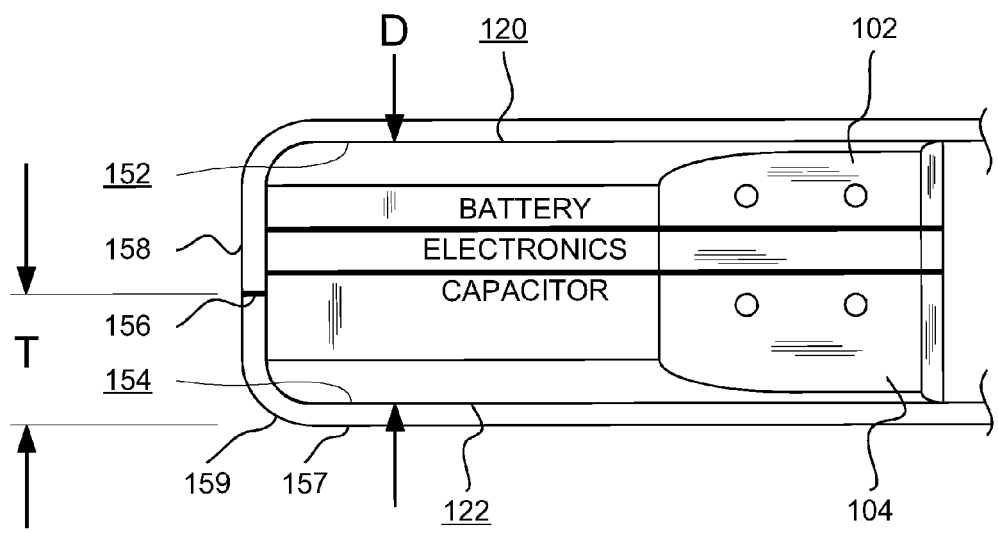
FIG. 1B illustrates a partial cross section of a device housing, a battery, an electronics module and a capacitor, according to one embodiment of the present subject matter.

FIG. 1B illustrates a partial cross section of a device housing, a battery, an electronics module and a capacitor, according to one embodiment of the present subject matter. In various embodiments, distance D extends between a first interior surface 152 for abutting a battery face 120, and a second interior surface 154 adapted for abutting surface 122. In various embodiments, the present subject matter selects a capacitor from a first index, and a battery from a second index, such that the combined thickness of the battery and the capacitor substantially matches the thickness D. Additionally, in various embodiments, the selection of battery thickness and capacitor thickness is made in light of the thickness of adhesive layer and/or insulative layers disposed between the battery and the electronics module, and the capacitor and the electronics module, and between these respective components and the device housing. In varying embodiments, the ratio between capacitor thickness and battery thickness is from about 7:1 to about 1.5:1. In additional embodiment, the ratio between the capacitor thickness and the battery thickness is from about 6:1 to about 2:1. Other ratios are possible without departing from the present subject matter.

In various embodiments, indexing of battery thickness, capacitor thickness, battery perimeter, capacitor perimeter, and other power source parameters is performed using a programmable computer. The present subject matter is not limited to indexes managed by programmable computers, however, as other indexing systems are within the scope of the present subject matter.

In addition to enabling adjustment of battery and/or capacitor thickness to a predetermined thickness, the present subject matter additionally allows for the adjustment of a device housing to a predetermined thickness. For example, some embodiments of the present subject matter use a housing which is formed and then trimmed. Some embodiments of the present subject matter include a first housing portion 158 which is mated to a second housing portion 157. In various embodiments, the second housing portion 157 is first formed such that it includes features such as curve 159. The second housing portion 157 is then trimmed to height "T". In various embodiments, enough scrap can be used when forming second housing portion 157 such that a wide range of thicknesses ("D") can be realized with reduced expenditures related to retooling.

In various embodiments of the present subject matter, a plurality of untrimmed housing portions are trimmed to different respective lengths. In various embodiments, these trimmed housing portions populate a plurality of trimmed housing portions. In some embodiments, at least two housing portions of the plurality of housing portions are indexed in a housing index. Various embodiments search the housing index for a housing portion which matches an application, and select the housing portion. For example, in some embodiments of the present subject matter, a stack of components has a thickness, and an index is searched for one or more housing portions which are mateable to the stack of components while minimizing the unused spaces in the housing in use. In various embodiments, the housing index is searchable. In some embodiments, a computer has an input of the thickness of components, and outputs which housing portions are to be selected based on that thickness.

In various embodiments, a plurality of housing portions have different respective depths or formed using other manufacturing processes, such as molding, cast, or other processes not disclosed expressly herein.

Figure 2:
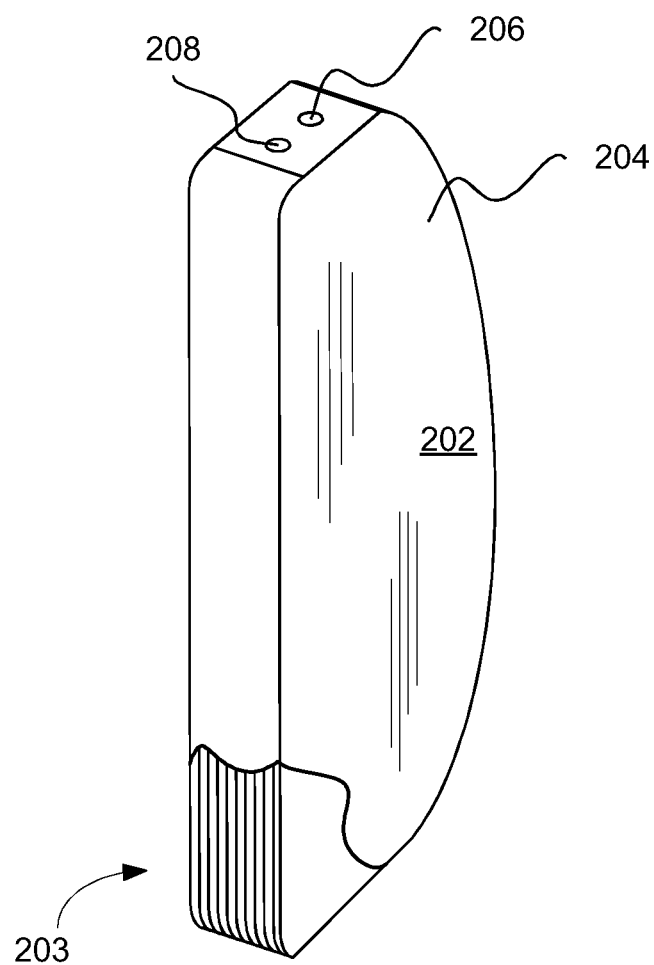
FIG. 2 is a perspective view of a capacitor, according to one embodiment of the present subject matter.

FIG. 2 is a perspective view of a capacitor, according to one embodiment of the present subject matter. The capacitor 204 is "D" shaped, but other shapes are contemplated by the present subject matter, as the illustrated embodiment, as well as discussions herein, do not present an exhaustive or exclusive list of embodiments. Other shapes may exclude pictured surfaces such as surface 202, resulting in a more rounded shape.

Substantially flat electrolytic capacitors, in various examples, include a plurality of capacitor layers 203 stacked together. In various embodiments, these one or more stacks of capacitors are assembled into a capacitor case. Various cases are conductive or nonconductive. Some cases include feedthroughs 206, 208 through which conductors pass. In some embodiments, electrodes of the capacitor are electrically connected to the case. The present subject matter includes, but is not limited to, embodiments disclosed on or around pages 12-37, 39, 41-140 of the following related and commonly assigned Provisional U.S. Patent Application "Method and Apparatus for Single High Voltage Aluminum Capacitor Design," Ser. No. 60/588,905, filed on Jul. 16, 2004, incorporated herein by reference.

In various embodiments, the present subject matter includes a flat electrolytic capacitor 204 with a planar capacitor surface 202. In various embodiments, the planar capacitor surface 202 includes a capacitor perimeter. In various embodiments, the capacitor stack is adapted to deliver between 7.0 Joules/cubic centimeter and 8.5 Joules/cubic centimeter. Some embodiments are adapted to deliver about 7.7 Joules/cubic centimeter. In some embodiments, the anode has a capacitance of between approximately 0.70 and 0.85 microfarads per square centimeter when charged at approximately 550 volts. In various embodiments, these ranges are available at a voltage of between about 410 volts to about 610 volts.

However, in some embodiments, the stack is disposed in a case, and linked with other components, a state which affects energy density in some embodiments. For example, in one packaged embodiment, including a case and terminals, the energy density available ranges from about 5.3 Joules per cubic centimeter of capacitor stack volume to about 6.3 Joules per cubic centimeter of capacitor stack volume. Some embodiments are adapted to deliver about 5.8 Joules. In various embodiments, these ranges are available at a voltage of between about 410 volts to about 610 volts.

Although these ranges embody one example possible within the scope of the subject matter, the subject matter is not so limited, and other capacitors without departing from the scope of the present subject matter.

Figure 3:
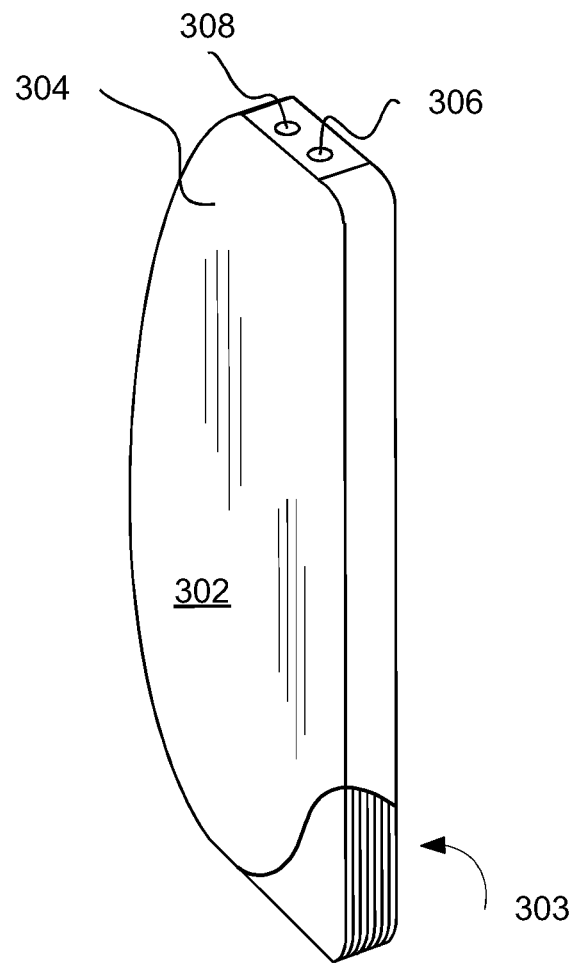
FIG. 3 is a perspective view of a battery, according to one embodiment of the present subject matter.

FIG. 3 is a perspective view of a battery, according to one embodiment of the present subject matter. In various embodiments, the battery 304 of the present subject matter is substantially flat. Substantially flat batteries, in various examples, include a plurality of battery electrodes 303 stacked together, and further assembled into a battery case. Various battery cases are conductive or nonconductive. Some battery cases include feedthroughs 306, 308. In some embodiments, an electrode of the battery is electrically connected to the case. In various embodiments, the battery cases include a planar battery surface 302. The present subject matter includes, but is not limited to, embodiments disclosed at paragraphs 0095-0110, 0136-0196, 0206-0258 of the following related and commonly assigned U.S. Patent Application, "Batteries Including a Flat Plate Design," U.S. patent application Ser. No. 10/360,551, filed on Feb. 7, 2003, incorporated herein by reference.

Figure 4:
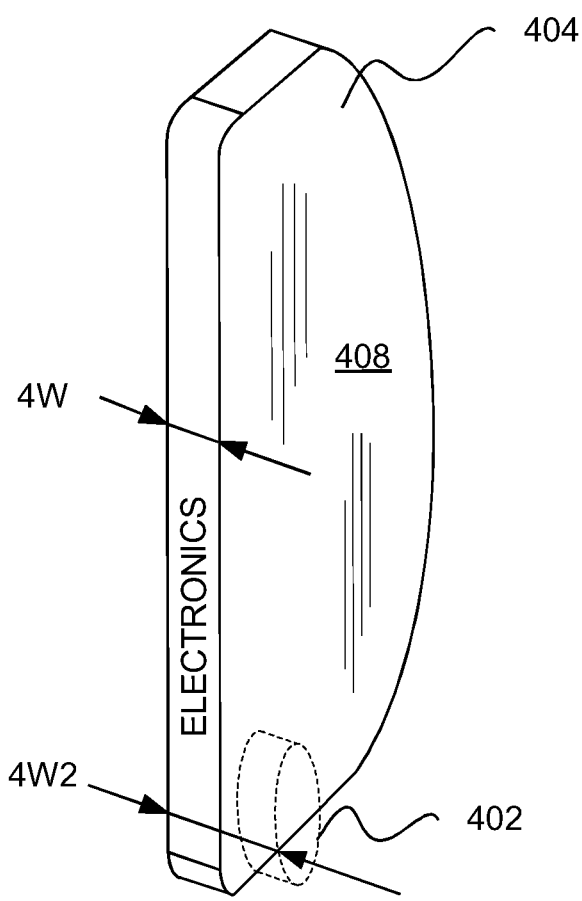
FIG. 4 is a perspective view of a battery and a capacitor, according to one embodiment of the present subject matter.

FIG. 4 is a perspective view of an electronics module 404, according to one embodiment of the present subject matter. In various embodiments, the electronics module 404 includes at least one face 408. In various embodiments, the face is planar, although other face contours, such as curved contours, or other nonlinear contours, are possible without departing from the scope of the present subject matter. Accordingly, it should be noted that some electronics module 404 layers do not include a planar face, but instead include a face which is adapted to mate to another component in an implantable device. The present subject matter includes, but is not limited an electronics modules 404 which are, planar, flexible, folded, and/or nonplanar in various embodiments.

In various embodiments, the electronics module includes a face which a power source is interface with. In various embodiments, the electronics face includes topography. In some embodiments, the topography is substantially planar. In some embodiments, the topography is nonplanar. In some embodiments, a power source which interfaces with the topography is equidistant from the topography, when the distance is measured orthogonally away from the electronics face. In some embodiments, the distance from the electronics face to the interfacing power source varies depending on where the distance is measured.

Some embodiments include one or more features which depart from a face of the electronics module 404. Some embodiments include one or more features which define an indentation in a face of the electronics module 404. The present subject matter includes, but is not limited to, embodiments in which a cylinder shape extends away from a face of the electronics module 404. Other embodiments exist, however, in which the feature is shaped otherwise. It should be noted that a feature does not necessarily exhibit a constant cross section along an axis extending away from a face orthogonally.

Some embodiments include a feature 402 which is a transformer. In some embodiments, the electronics module 404 has a first thickness 4 W, measured orthogonally away from a first planar face. In additional embodiments, the electronics module includes a feature which extends away from the first planar face a thickness of 4 W 2, measured orthogonally away from an electronics face. In various embodiments, the second thickness 4 W 2 is less than the first thickness 4 W. In additional embodiments, the second thickness is greater than the first thickness 4 W. Some embodiments are contemplated in which the first thickness 4 W is substantially equivalent to the second thickness 4 W 2. Embodiments are contemplated in which multiple features extend away from one or more faces at equivalent thicknesses. Embodiments are additionally contemplated in which multiple features extend away from one or more faces at different thicknesses.

In various embodiments, a plate which is shaped to match face 408 is adapted to accommodate feature 402. For example, some embodiments include a cut out which is adapted to receive feature 402. Some embodiments include a cut into the side of a layer to be mated to the electronics module 404. Additional embodiments include a cut-out which is inside the overall perimeter of the layer to be matted the electronics module 404. Additionally, it should be noted that the present subject matter is not limited to embodiments in which the electronics module 404 has a major face 408 on which a feature 402 is located, as other configurations, including configuration in which a feature does not extend from a substantially planar face, are within the scope of the present subject matter.

Figure 5:
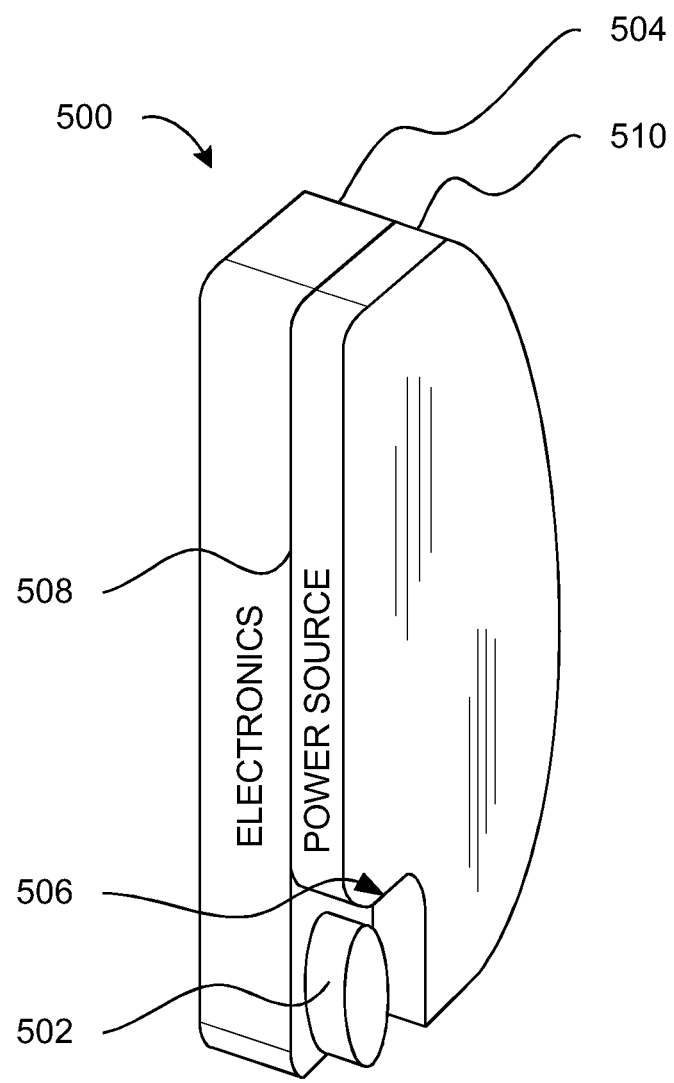
FIG. 5 is a perspective view of electronics and a power source, according to one embodiment of the present subject matter.

FIG. 5 is a perspective view of electronics and a power source, according to one embodiment of the present subject matter. The electronics 504 are mated to a power source 510. In various embodiments, two components are in a stack 500 and are mated along an interface 508. In various embodiments, the electronics include a feature 502. In some embodiments, the feature 502 is a transformer. In various embodiments, the power source 510 includes a void 506 which is adapted to receive the feature 502 while the power source 510 and the electronics 504 are in a stack 500.

In various embodiments, the power source 510 is a battery. In some embodiments, the power source 510 is a capacitor. In various embodiments, the power source 510 includes a stack of substantially planar layers which are shaped to define the void 506. Although a power source 510 is illustrated which exhibits a consistent cross section as it extends away from interface 508, the present subject matter is not so limited. The present subject matter includes other power source shapes which do not include a constant cross section as the power source extends away from interface 508 orthogonally.

Figure 6:
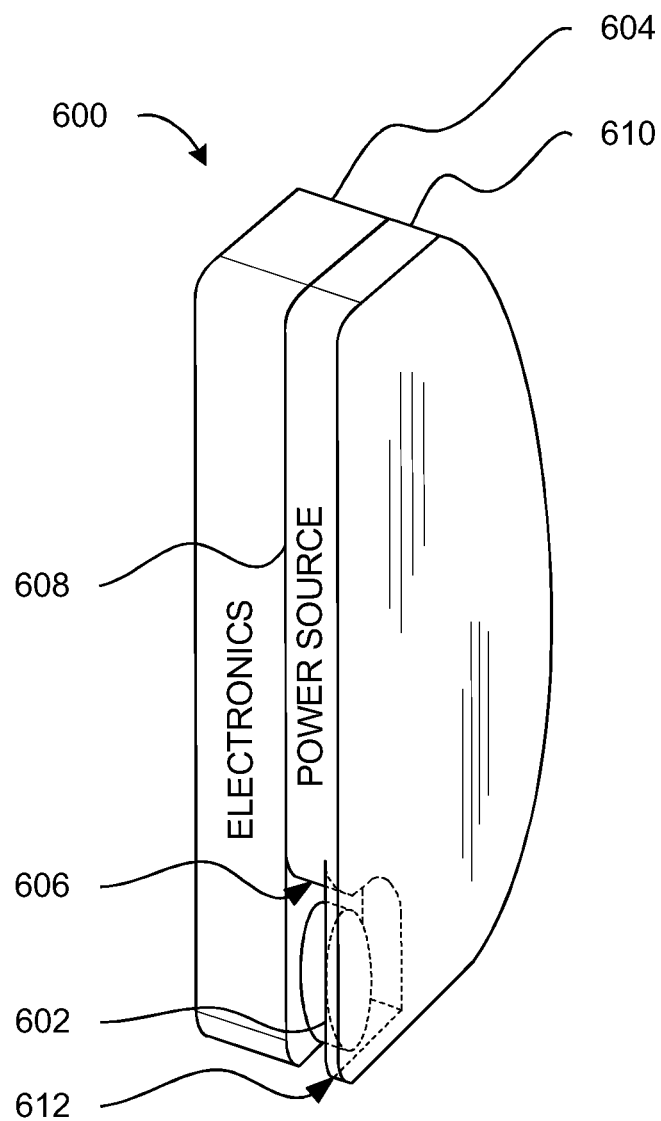
FIG. 6 is a perspective view of electronics and a power source, according to one embodiment of the present subject matter.

FIG. 6 is a perspective view of electronics and a power source, according to one embodiment of the present subject matter. The electronics 604 are mated to a power source 610. In various embodiments, two components are in a stack 600 and are mated along an interface 608. In various embodiments, the electronics include a feature 602. In some embodiments, the feature 602 is a transformer. In various embodiments, the power source 610 includes a void 606 which is adapted to receive the feature 602 while the power source 610 and the electronics 604 are in a stack 600.

In various embodiments, the power source 610 is a battery. In some embodiments, the power source 610 is a capacitor. In various embodiments, the power source 610 includes a stack of substantially planar layers which are shaped to define the void 606. Although a power source 610 is illustrated which exhibits a consistent cross section as it extends away from interface 608, the present subject matter is not so limited. The present subject matter includes other power source shapes which do not include a constant cross section as the power source extends away from interface 608 orthogonally.

The present illustrations shows a power source which does not have a uniform cross section as it extends orthogonally away from the interface 608. The illustrated power source 610 includes a shelf 612 which extends over the feature 602 and which opposes portions of electronics 604 which are under and which support feature 602.

In various embodiments, the power source 608 includes a stack of substantially planar layers. In various embodiments, these layers are shaped differently to define void 606. at least one or more of the layers of the power source define shelf 602, in various embodiments. The present subject matter, as such, allows for an adjustable thickness power source 610 which can accommodate one or more features simply by stacking more or less electrode layers, and providing a case for those electrode layers which is shaped to accommodate those layers.

The present subject matter includes various processes for making and using a component of the present subject matter. In one embodiment of the present subject matter, a process includes establishing form factor and power capacity requirements for a power source to be used in an implantable medical device. The embodiment includes constructing a flat battery by stacking flat battery layers into a battery stack and positioning the stack in a battery case with a planar interface and a battery perimeter and battery thickness. The embodiment further includes constructing a flat electrolytic capacitor by stacking flat capacitor layers into a capacitor stack and positioning the stack in a capacitor case with a planar interface and a capacitor perimeter and capacitor thickness. The embodiment additionally includes layers the flat battery and the flat electrolytic capacitor with an electronics module. Embodiments are included in which a battery perimeter is substantially coextensive with an electronics module perimeter. Embodiments are additionally contemplated in which a capacitor perimeter is substantially coextensive with an electronics module perimeter. These embodiment is illustrative of the present subject matter, but it should be noted that other combinations of steps, and additional steps, also lie within the scope of the present subject matter.

Embodiments are included which encapsulate the stack with at least a first housing portion and a second housing portion. In various embodiments, the first housing portion opposes the second housing portion. In various embodiments the first housing portion is a cup, and the second housing portion is a lid. In some embodiments, the first housing portion is a cup with a first cup mouth, and the second housing portion is a cup with a second cup mouth. In various embodiments, the first cup mouth conforms to the second cup mouth and is sealed to the second cup mouth with a seal. A seal includes a laser weld, in various embodiments. The laser weld occurs at a butt joint, a step joint, a lap joint, and/or other joints, in various embodiments. In various embodiments, the seal is hermetic.

In various embodiments, the first housing portion and the second housing portion at least partially define an interior. In various embodiments, the battery, capacitor, and electronics module are disposed in the interior. In various embodiments, additional components are disposed in the interior.

Embodiments are included in which the first housing portion is trimmed based on a thickness of a stack disposed in the interior. In various embodiments, the stack includes the battery, the capacitor, and the electronics module, stack unto one another. In various embodiments, the battery and the capacitor sandwich the electronics module. In various embodiments, the stack is composed of components which are layered onto one another along a vector which runs orthogonally between the first housing portion and the second housing portion. In various embodiments, the vector is orthogonal to a first interior face of the first housing portion, and a second interior face of the second housing. In various embodiments, the first interior face is substantially planar. In various embodiments, the second interior face is substantially planar. In some embodiments the second housing portion is trimmed. In various embodiments, both the first and second housing portions are trimmed.

In some embodiments, a battery thickness, battery perimeter, capacitor thickness and capacitor perimeter are selected based on form factor and power capacity requirements for an implantable medical device. Additionally, various method embodiments include measuring a ratio between battery thickness and capacitor thickness, and using this ratio in selecting a battery and capacitor. A ratio is be established by known power requirements, in various embodiments. Another example combines size requirements with power requirements in selecting a ratio. The ratio can be stored and used by a design process or manufacturing process to discern the mechanical and electrical composition of a needed power source, in various embodiments.

In various embodiments, the present subject matter includes delivering from the flat battery and the flat electrolytic capacitor from about 1.25 Joules per Amp hour of battery capacity to about 50 Joules per amp hour of battery capacity. In some of these embodiments, the flat battery has a battery capacity density of from about 0.23 amp hours per cubic centimeter of flat battery to about 0.25 amp hours per cubic centimeter of flat battery. Battery capacity density is measured by dividing the amp-hour rating of the battery by the battery volume, in various embodiments. The present subject matter includes, but is not limited to, embodiments disclosed at paragraphs 0095-0110, 0136-0196, 0206-0258 of the following related and commonly assigned U.S. Patent Publication, "Batteries Including a Flat Plate Design," U.S. Patent Publication No. 2004/0127952, filed on Feb. 7, 2003, incorporated herein by reference.

In additional embodiments, the flat electrolytic capacitor includes an energy density of from about 4.65 joules per cubic centimeter of flat electrolytic capacitor to 6.5 joules per cubic centimeter of flat electrolytic capacitor. The present subject matter includes, but is not limited to, embodiments disclosed on or around pages 12-37, 39, 41-140 of the following related and commonly assigned Provisional U.S. Patent Application "Method and Apparatus for Single High Voltage Aluminum Capacitor Design," Ser. No. 60/588,905, filed on Jul. 16, 2004, incorporated herein by reference.

Embodiments are contemplated in which a power source form factor is known, and in which a device housing is trimmed to fit the power source form factor. For example, in some embodiments, a performance specification requires a predetermined number of capacitor electrodes to be stacked into a power source and then stacked onto an electronics module. Some embodiments include a performance specification which requires a predetermined number of battery electrodes to be stacked into a power source and then onto an electronics module. In various embodiments, a process is able to determine the overall thickness of one or more power sources, combined with an electronics module. In some of these embodiments, the present subject matter tailors a device housing to this overall thickness. In some of these embodiments, this is done by drawing one or more housing portions, and then trimming these housing portions. Because of the nature of a drawing process, various embodiments are able to provide housings of different depths with reduced tooling expenses. A further benefit is a reduced time to retool. Another benefit is the provision of a retooling process which provides improved adjustability.

In various embodiments, electrode machinery is tooled to form an electrode of a specific size and shape. In some embodiments, a substantially planar electrode is punched out of a sheet. In some embodiments, the sheet is on a roll. Batteries and capacitors of different capacities require more or less surface area. One way to add surface area is to increase a punch perimeter of an electrode. However, such changes to tooling can be cost intensive, therefore it is beneficial to pursue an alternative route to increasing surface area. One alternative is to increase the number of layers in a stack. The present subject matter allows for easy adjustment to stack height by enabling device housing changes which can accommodate a range of stack heights with reduced tooling changes. For example, in one embodiment, a power source capacity is increased by adding layers to a stack of that power source. To accommodate the new power source size, various embodiments change the trim height of a device housing. The device housing can be made deeper by using the same workpiece which is a product of a drawing operation, and changing the height at which the workpiece is trimmed. In another embodiment, the number of capacitor foil layers are reduced. At the same time, the number of battery electrode layers are increased. The device housing does not have to be adjusted to accommodate the changes.

Various methods of the present subject matter benefit from selecting capacitor stack layers and battery stack layers which are substantially parallel to an interface with another component. By constructing the power source as such, various benefits are possible. For example, in one embodiment, a single two-axis machine can position capacitor layers in a stack, position the capacitor stack in a capacitor case, position battery layers in a stack, and position the battery stack in a battery case. In one embodiment, the single two-axis machine is a pick-and-place machine. This combination is provided for illustration, but other combinations of these steps are possible, and additional steps are also within the scope of the present subject matter.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments, and other embodiments will be apparent to those of skill in the art upon reviewing the above description. The scope of the present subject matter should be determined with reference to the appended claims, along with the full scope of equivalents to which such claims are entitled.

What is claimed is:

1. An apparatus comprising:
    an implantable device housing, the implantable device housing defining an interior;
    a stack disposed within the interior of the implantable device housing, the stack including:
        a first case distinct from the implantable device housing;
        a first component within the first case;
        a second case distinct from the implantable device housing and the first case;
        a second component within the second case;
        a third component within a third case, the third case disposed between, and aligned with, the first and second cases; and
        a separator disposed between the third case and one of the first case or the second case;
    wherein the third case includes a first substantially planar face adjacent to and coextensive with a first substantially planar face of the first case;
    wherein the third case includes a second face opposite the first planar face of the third case, the second planar face of the third case including a substantially planar portion adjacent to, and coextensive with, a first substantially planar face of the second case;
    wherein at least one of the first, second or third cases includes a first power source;
    wherein at least one of the first, second or third cases includes a second power source;
    wherein at least one of the first, second or third cases includes an electronics module, the electronics module configured to generate electrical pulses using the first power source;
    wherein a ratio of a thickness of the first power source to a thickness of the second power source is between about 7:1 and about 1.5:1; and
    wherein a thickness of the interior of the housing is configured to substantially match a thickness of the stack.

2. The apparatus of claim 1, wherein the first power source is a capacitor.

3. The apparatus of claim 2, wherein the second power source is a battery.

4. The apparatus of claim 3, wherein the battery and the capacitor are adapted to deliver from about 1.25 Joules per Amp hour of battery capacity to about 50 Joules per amp hour of battery capacity.

5. The apparatus of claim 4, wherein the battery includes a battery capacity density of from about 0.23 amp hours per cubic centimeter to about 0.25 amp hours per cubic centimeter.

6. The apparatus of claim 4, wherein the capacitor includes an energy density of from about 4.65 joules per cubic centimeter to 6.5 joules per cubic centimeter.

7. The apparatus of claim 1, wherein the third component includes the electronics module, and wherein the second face of the third case includes a topography which, along the second face, varies in orthogonal distance from the first substantially planar face of the third case.

8. The apparatus of claim 1, wherein the substantially planar portion of the third case is a first orthogonal distance from the first substantially planar face of the third case, and a transformer extends a second orthogonal distance from the first substantially planar face of the third case, the second orthogonal distance being greater than the first orthogonal distance.

9. The apparatus of claim 1, wherein the first component includes a battery, and the second component includes a capacitor and further comprising:
    a battery face of the first case opposed to the first face of the first case, with a battery sidewall extending between the battery face and the first face of the first case; and
    a first capacitor face opposed to a first face of the second case, with a capacitor sidewall extending between the first capacitor face and the first face of the second case,
    wherein the battery sidewall and the capacitor sidewall define a substantially continuous surface.

10. The implantable medical device of claim 1, wherein the first power source includes a first plurality of substantially planar electrodes; and
    wherein the second power source includes a second plurality of substantially planer electrodes.

11. The apparatus of claim 10, wherein the first plurality of substantially planar electrodes include at least two different shapes.

12. The apparatus of claim 10, wherein the second plurality of substantially planar electrodes include at least two different shapes.

13. The apparatus of claim 10, wherein the first plurality of substantially planar electrodes are disposed parallel the planar first power source face.

14. The apparatus of claim 13, wherein the second plurality of substantially planar electrodes are disposed parallel the second electronics face.

* * * * *